United States Patent [19]

Kubba

[11] 4,014,864
[45] Mar. 29, 1977

[54] HETEROCYCLIC SUBSTITUTED AZO DYESTUFF

[75] Inventor: Ved Parkash Kubba, Bombay, India

[73] Assignee: Ciba-Geigy Corporation, Ardsley, N.Y.

[22] Filed: Feb. 13, 1976

[21] Appl. No.: 657,776

[30] Foreign Application Priority Data

Feb. 25, 1975 Switzerland .............. 2374/75

[52] U.S. Cl. .............. 260/157; 260/158; 260/306; 260/306.6 R
[51] Int. Cl.² .............. C07D 277/04; C09B 29/36; C09B 49/06; C07D 233/02
[58] Field of Search .... 260/157, 158, 306, 306.6 R

[56] References Cited

UNITED STATES PATENTS

| | | | |
|---|---|---|---|
| 3,246,004 | 4/1966 | Hall et al. | 260/306.6 R X |
| 3,592,807 | 7/1971 | von Brachel et al. | 260/158 X |
| 3,595,852 | 7/1971 | Hahn et al. | 260/158 |
| 3,840,517 | 10/1974 | Weaver et al. | 260/158 X |
| 3,971,771 | 7/1976 | Angliken et al. | 260/158 X |

FOREIGN PATENTS OR APPLICATIONS

| | | | |
|---|---|---|---|
| 643,681 | 9/1950 | United Kingdom | 260/306 R |
| 1,351,375 | 4/1975 | United Kingdom | 260/158 |

*Primary Examiner*—Allen B. Curtis
*Attorney, Agent, or Firm*—Karl F. Jorda; Edward McC. Roberts; Prabodh I. Almaula

[57] ABSTRACT

An azo compound that is free from sulphonic acid groups of the formula

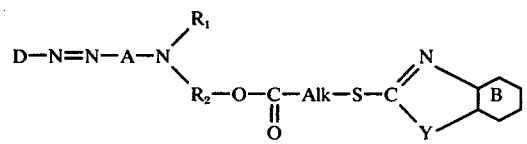

in which D represents the radical of a diazo component, A represents an optionally substituted, 1,4-phenylene radical, $R_1$ represents an optionally substituted alkyl radical, $R_2$ represents an optionally substituted alkylene radical, Alk represents an alkylene radical of 1–4 carbon atoms and Y represents an imino group, a sulphur atom or an oxygen atom and ring B may be substituted by bromine, fluorine, chlorine atoms, cyano, nitro, trifluoromethyl, alkyl, alkoxy, acylamino, acyloxy, carbalkoxy, optionally N-alkylated carbamoyl and optionally N-alkylated sulphamoyl groups and by a benzo residue. The compounds dye polyester fibres in yellow, red or blue shades with good fastness.

16 Claims, No Drawings

HETEROCYCLIC SUBSTITUTED AZO DYESTUFF

The invention provides valuable new azo compounds that are free from sulphonic acid groups and have the formula

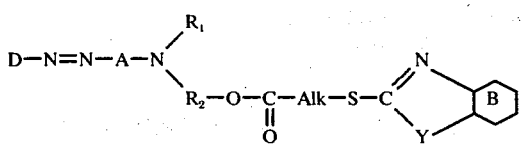

in which D represents the radical of a diazo component, A represents an optionally substituted, 1,4-phenylene radical, $R_1$ represents an optionally substituted alkyl radical, $R_2$ represents an optionally substituted alkylene radical, Alk represents an alkylene radical of 1–4 carbon atoms and Y is an optionally substituted imino group, a sulphur atom or an oxygen atom and the aromatic or partially or wholly saturated ring B may have further substituents such, for example, as halogen atoms, nitro groups, or organic substituents.

According to the invention the compounds are obtained by coupling a diazonium compound of a diazo component with a coupling component of the formula

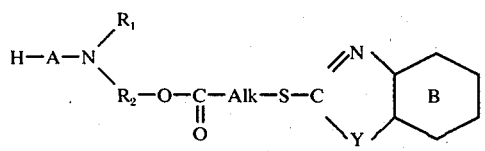

wherein A, $R_1$, $R_2$, Alk and Y have the above-defined meanings, and treating the resulting azo dyestuffs optionally with quaternising agents.

Of particular interest are compounds that are free from sulphonic acid groups of the formula

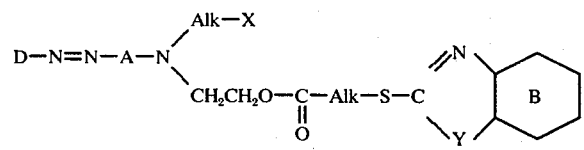

in which D, A, Alk and Y have the same meanings as above and X is a hydrogen atom, a hydroxy group, a halogen atom, a cyano group or an organic radical, preferably an alkoxy, acyloxy, aroyloxy or an alkyl radical.

Particularly, preferred are the compounds of the formula

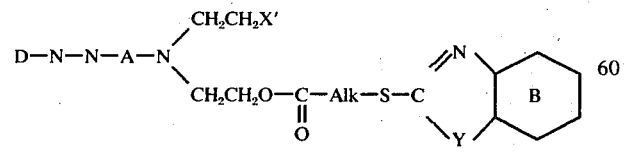

in which D, A, Alk and Y have the same meanings as above and X' is an alkoxy or acyloxy radical of an organic acid, a lower alkyl radical or a hydrogen atom, hydroxy group or a cyano group. X' may represent, for example, a methyl, ethyl, propyl, butyl, radical, an acyloxy radical of a carboxylic acid, such as formic, acetic, propionic, butyric acid, also, optionally substituted benzoic acid and the ring B may have further substituents such as halogen atoms, nitro groups or organic substituents.

The acyloxy radical X' could also be the radical of a carboxylic acid containing preferably up to 19 carbon atoms, for example dodecyl carbonyl, stearyl, phenylacetyl, cinnamoyl, oleyl, substituted aroyloxy groups such as p-carboxymethylbenzoyl, 2-furancarbonyl, 2-pyridinecarbonyl, 2-thiophenecarbonyl radicals. Other suitable acyl groups are the acyl radicals of carbamic acids and of carbonic acid half ester 20 as methylamino carbonyl, phenylaminocarbonyl, n-butylaminocarbonyl, p-tosylaminocarbonyl, ethyloxycarbonyl, phenoxycarbonyl and benzyloxy carbonyl radicals.

In the preceding formulae, the ring B may be substituted by bromine, fluorine, chlorine atoms, cyano groups, nitro groups, trifluoromethyl, alkyl groups, such as methyl and ethyl groups, alkoxy groups, such as methoxy and ethoxy groups, acylamino groups, such as fatty acid acylamino groups, for example formylamino, acetylamino, propionylamino or butyrylamino groups, and benzoylamino groups, optionally N-alkylated sulphamoyl groups as well as 1,2-benzo residue.

The $R_1$ which represents an alkyl group or a substituted alkyl group may be for example, a lower alkyl group with 1–4C atoms or a substituted alkyl group, for example β-chloro-ethyl, β, β, β-trifluoroethyl, β-γ-dichloropropyl, alkylphenyl, for example benzyl, β-phenethyl, halogenated alkyl groups, for example β-chloroethyl, β-β, β,-trifluoroethyl, β,γ-dichloropropyl or 3-chloro-2hydroxypropyl, β-cyanoethyl, alkoxyalkyl, for example β-ethoxyethyl, or β-methoxybutyl, hydroxyalkyl, for example β-hydroxyethyl, β-γ-dihydroxypropyl, nitroalkyl, for example β-nitroethyl, acylaminoalkyl, for example β-(acetyl or formyl)-aminoethyl, fatty acid acyloxyalkyl, for example formyloxyalkyl, β-acetyloxyethyl, β,γ-diacetoxypropyl and β-butyryloxypropyl, β-(alkyl or aryl)-sulphonylethyl, vinylsulphonylalkyl, phenylsulphonylalkyl and β,(chlorobenzenesulphonyl)-ethyl, alkyl- or arylcarbamoyloxyethyl and β-methylcarbamyloxyethyl, butylcarbamyloxyethyl and β-phenylcarbamyloxyethyl, alkyl- or aryloxycarbonyloxyalkyl, for example o-, m- or p-(methoxy, ethoxy,β'chloroethoxy, isopropyloxy or methyl)-phenyl-carbonyloxy-ethyl, γ-acetamidopropyl, β-(p-nitrophenoxy)-ethyl, β-(p-hydroxyphenoxy)-ethyl, β-(-acetylethoxycarbonyl)-ethyl, β-(β'-cyano, hydroxy, methoxy or acetoxy)-ethoxycarbonylethyl, cyanoalkyloxyalkyl, 2-carboxyethyl, β-acetylethyl, 2-diethylaminoethyl, β-cyanoacetoxyethyl, β-cyanoacetoxyethyl, β-benzoyloxyethyl and β-(p-alkoxy- or phenoxy-benzoyl)-oxyethyl groups.

The radical $R_2$ represents an alkylene radical containing not more than 3 carbon atoms. The group A corresponds advantageously to the formula

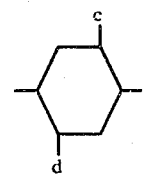

wherein c is in the ortho position to the amino group and d is in the ortho position to the azo group.

The radicals c and d represent hydrogen atoms, chlorine atoms, lower alkyl or alkoxy radicals, such as the methyl, ethyl, methoxy or ethoxy radicals, also phenylthio or phenoxy radicals.

The radical d may also represent in addition a bromine atom, a trifluoromethyl group and an acylamino group that is optionally alkylated, preferably methylated, at the nitrogen atom, in which the acyl radical is the radical of a carboxylic acid such as a formyl, acetyl, propionyl, butyryl, or benzoyl radical, the radical of an organic monosulphonic acid, such as, methane, ethane or p-toluene-sulphonic acid or the radical of a carbonic acid monoester or carbonic acid amide such as methoxycarbonyl, phenoxycarbonyl, aminocarbonyl and butylamino carbonyl.

The diazo radical D is derived principally from mono or bicyclic amine of the formula

D-NH$_2$ such as any kind of diazotisable amine that contains no sulphonic acid groups, but is derived especially from amines that possess a heterocyclic 5-membered ring with 2 or 3 hetero atoms, chiefly a nitrogen atom and one or two sulphur, oxygen, or nitrogen atoms as hetero atoms, and from aminobenzenes (i.e. aminobenzenes that have substituents with a negative sigmapara value according to the Hammet equation), in particular those of the formula

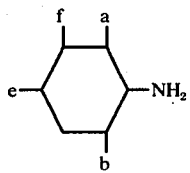

in which a represents a hydrogen or halogen atom, an alkyl or alkoxy, nitro, cyano, carbalkoxy or alkylsulphenyl group, b represents a hydrogen or halogen atom, an alkyl, cyano or trifluoromethyl group, e represents a nitro, cyano, carbalkoxy, optionally substituted sulphonamide or alkylsulphonyl group, f represents a hydrogen or halogen atom, a carbalkoxy or carboxylic acid amide group.

As example these may be mentioned:

2-aminothiazole,
2-amino-5-nitrothiazole,
2-amino-5-methylsulphonyl-thiazole,
2-amino-5-cyanothiazole,
2-amino-4-methyl-5-nitrothiazole,
3-amino-benzisothiazole,
3-amino-5-chloro-benzisothiazole,
3-amino-5-nitro-7-chloro-benzisothiazole
3-amino-5-chloro-7-bromo-benzisothiazole
3-amino-5, 7-dibromo-benzisothiazole
2-amino-4-methylthiazole,
2-amino-4-(4'-chloro)-phenylthiazole,
3-aminopyridine,
3-aminoquinoline,
3-aminopyrazole,
3-amino-1-phenylpyrazole,
2-amino-4-phenyl thiazole
2-amino-4-(4'-nitro)-phenylthiazole
3-aminoindazole,
3-amino-1,2,4-triazole,
5-(methyl-, ethyl-, phenyl- or benzyl)-1,2,4-triazole,
3-amino-1-(4'-methoxyphenyl)-pyrazole,
2-aminobenzthiazole,
2-amino-6-methylbenzthiazole,
2-amino-6-methoxybenzthiazole,
2-amino-6-cyanobenzthiazole,
2-amino-6-thiocyanobenzthiazole,
2-amino-6-nitrobenzthiazole,
2-amino-6-carboethoxybenzthiazole,
2-amino-(4- or 6)-methylsulphonylbenzthiazole,
2-amino-1,3,4-thiadiazole,
2-amino-1,3,5-thiadiazole,
2-amino-4-phenyl- or -4-methyl-1,3,5-thiadiazole,
2-amino-5-phenyl-1,3,4-thiadiazole,
2-amino-3-nitro-5-methylsulphonyl-thiophene,
2-amino-3,5-bis-(methylsulphonyl)-thiophene,
5-amino-3-methyl-isothiazole,
2-amino-4-cyano-pyrazole,
2-(4'-nitrophenyl)-3-amino-4-cyanopyrazole,
3- or 4-aminophthalimide,
aminobenzene, 1-amino-2-trifluoromethyl-4-chlorobenzene,
1-amino-2-cyano-4-chlorobenzene,
1-amino-2-carbomethoxy-4-chlorobenzene,
1-amino-2-carbomethoxy-4-nitrobenzene,
1-amino-2-chloro-4-cyanobenzene,
1-amino-2-chloro-4-nitrobenzene,
1-amino-2-bromo-4-nitrobenzene,
2-amino-6-chlorobenzthiazole.
1-amino-2-chloro-4-carbothoxybenzene,
1-amino-2-chloro-4-methylsulphonylbenzene,
1-amino-2-methylsulphonyl-4-chlorobenzene,
1-amino-2, 4-dinitro-6-methylsulphonylbenzene,
1-amino-2, 4-dinitro-6-(2'-hydroxyethylsulphonyl)-benzene,
1-amino-2, 4-dinitro-6-(2'-chloroethylsulphonyl)-benzene,
1-amino-2-methylsulphonyl-4-nitrobenzene,
1-amino-2, 4-dinitrobenzene,
1-amino-2, 4-dicyanobenzene,
1-amino-2-cyano-4-methylsulphonylbenzene,
1-amino-2, 6-dichloro-4-cyanbenzene,
2-cyano-4-chloroaniline,
2-cyano-4-chloro-6-bromaniline,
2-cyano-4, 6-dibromaniline,
1-amino-2, 6-dichloro-4-nitrobenzene,
1-amino-2, 4-dicyano-6-chlorobenzene,
4-amino-benzoic acid cyclohexyl ester,
1-amino-2, 4-dinitro-6-chlorobenzene and especially
1-amino-2-cyano-4-nitrobenzene, also
1-aminobenzene-2, -3- or -4-sulphonic acid amide, such as
N-methyl- or N,N-dimethyl- or diethylamide,
N, γ-isopropyloxypropyl-2-aminophthalene-6-sulphonic acid amide,
N, γ, isopropyloxypropyl-1-aminobenzene-2-, -3- or -4-sulphonic acid amide,
N-isopropyl-1-aminobenzene-2-, -3- or -4-sulphonic acid amide,
N, γ-methoxypropyl-1-aminobenzene-2-, -3- or -4-sulphonic acid amide,
N,N-bis-(β-hydroxyethyl)-1-aminobenzene-2-, -3- or -4-sulphonic acid amide,
1-amino-4-chlorobenzene-2-sulphonic acid amide, and the N-substituted derivatives, 2-, 3- or 4-aminophenylsulphamate,
2-amino-4-, -5- or -6-methylphenylsulphamate,
2-amino-5-methoxy-phenylsulphamate,
3-amino-6-chlorophenylsulphamate,
3-amino-2, 6-dichlorophenylsulphamate,
4-amino-2- or -3-methoxyphenylsulphamate,
N,N-dimethyl-2-aminophenylsulphamate,
N,N-di-n-butyl-2-aminophenylsulphamate,
N,N-dimethyl-2-amino-4-chlorophenylsulphamate,
N,n-propyl-3-aminophenylsulphamate,
N,N-di-n-butyl-3-aminophenylsulphamate,
O(3-aminophenyl)-N-morpholino-N-sulphonate,
O(3-aminophenyl)-N-piperidine-sulphonate,
N-cyclohexyl-O-(3-aminophenyl)-sulphamate:
N(N-methylaniline)-O-(3-aminophenyl)-sulphamate,
N,N-diethyl-3-amino-6-methylphenyl-sulphamate,
N-ethylenimine-O-(4-aminoohenyl)-sulphamate,
N,N-dimethyl-4-aminophenylsulphamate,
O-(n-propyl)-O-(3-aminophenyl)-sulphamate,
O,β-chloroethyl-O-(2-aminophenyl)-sulphamate,
O-benzyl-O-(3-aminophenyl)-sulphanate and
O-ethyl-O-(4-amino-2,6-dimethyl-phenyl)-sulphonate,
4-aminoazobenzene,
3,2'-dimethyl-4-aminoazobenzene,
2-methyl-5-methoxy-4-aminoazobenzene,
4-amino-2-nitroazobenzene,
2,5-dimethoxy-4-aminoazobenzene,
4'-methoxy-4-aminoazobenzene,
2-methyl-4'-methoxy-4-aminoazobenzene,
3,6,4'-trimethoxy-4-aminoazobenzene,
4'-chloro-4-aminoazobenzene
2'-or 3'-chloro-4-aminoazobenzene,
3-Nitro-4-amino-2', 4'-dichloroazobenzene and
4-aminoazobenzene-4'-sulphonic acid amide.

Instead of the above cited diazo components that are free from ionogenic water-solubilising groups, it is also possible to use those that contain fibre reactive groups such for example, as s-triazinyl radicals that carry 1 or 2 chlorine or bromine atoms on the triazine ring pyrimidyl radicals that carry 1 or 2 arylsulphonyl or alkanesulphonyl groups on the pyrimidine ring, mono- or bis-)γ-halogeno-β-hydroxypropyl)-amino groups, β-halogeno ethylsulphamyl radicals, β-halogeno-ethoxy groups, β-halogeno-ethylmercapto groups, 2-chloro-benzthiazolyl-6-azo groups, 2-chlorobenzthiazolyl-6-amino groups, γ-halogeno-β-hydroxy-propylsulphamyl radicals, chloroacetylamino groups, α,β-dibromo-propionyl groups, vinylsulphonyl groups and 2,3-epoxypropyl groups.

Suitable fibre reactive diazo components are, for example:

N,β-chloroethyl-3-chloro-4-amino-benzenesulphamide (hydrochloride),
N,β-chloroethyl-4-aminobenzene-sulphamide (hydrochloride)
3-bromo-4-amino-β-chloroacetophenone,
N,γ-chloro-β-hydroxypropyl-4-aminobenzene-sulphamide,
N,β-chloroethyl-1-amino-4-naphthylsulphonamide,
N,β-chloroethyl-1-amino-3, 5-dichloro-benzenesulphamide and
4-(γ-chloro-β-hydroxy-propoxy) aniline.

Suitable quaternized diazo components are, for for example:

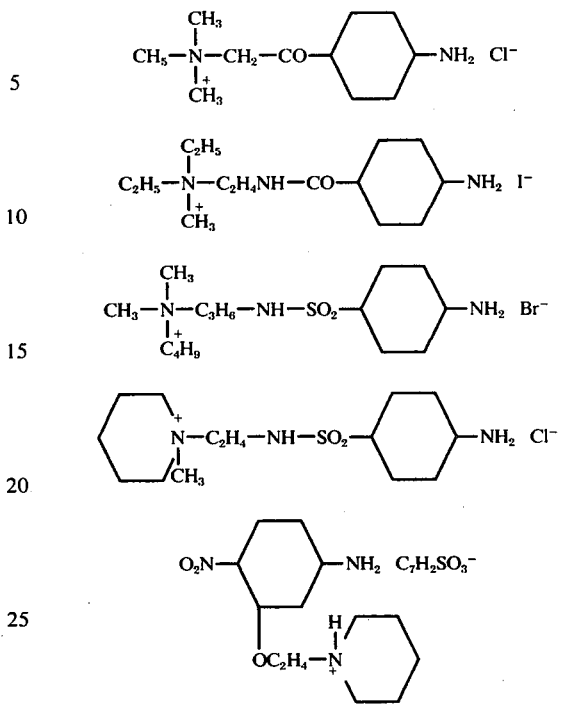

The coupling component is obtained by condensing halogenated fatty acid chloride with hydroxyalkyl anilines which are optionally substituted at the aromatic nucleus. The reaction may be carried out in an inert organic solvent optionally in the presence of an acid acceptor, for example, a tertiary amine, to give intermediates of the formula

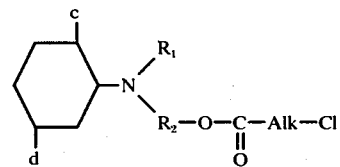

in which c, d, R₁, R₂ and Alk have the earlier defined meanings.

These intermediates are further condensed with the sodium salt of optionally substituted 2-mercapto-benzthiazoles, benzoxazoles and benzimidazoles in alcohol or in an inert organic solvent admixed with dimethylformamide at their boiling temperature and worked up in the usual manner to furnish the desired coupling components, having the formula

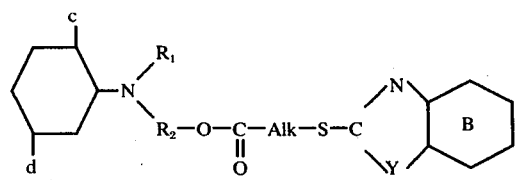

in which c, d, R₁, R₂, Alk and Y have the same meaning as above.

Suitable coupling components containing the group

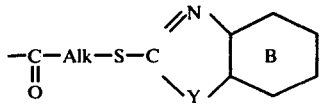

are, for example, the tertiary amines of the formula

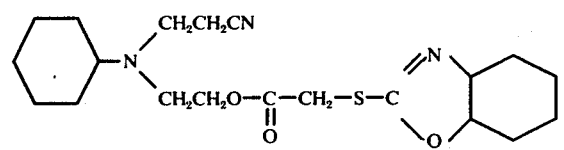

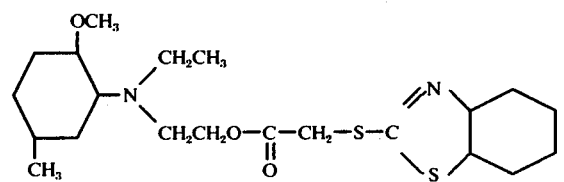

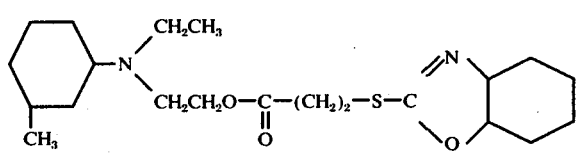

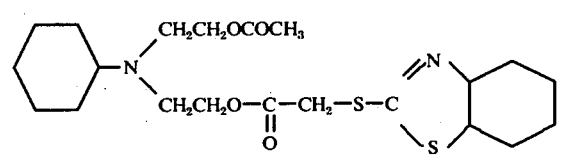

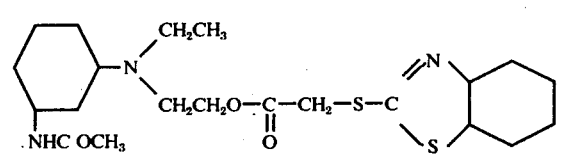

Diazotisation of diazo components may be carried out by known methods, for example, with the aid of a mineral acid and sodium nitrite or, for example, with a solution of nitrosyl sulphuric acid in concentrated sulphuric acid.

Coupling may likewise be carried out in known manner, for example, in neutral to acid medium, if necessary, in the presence of sodium acetate or similar buffer which influences the rate of coupling or a catalyst for example, pyridine, or a salt thereof. After coupling, the dyestuff formed may easily be isolated from the coupling mixture, for example, by filtration, because it is virtually insoluble in water.

Heterocyclic diazo components that possess a quaternisable nitrogen atom can also coupled in N-alkylated form.

Those of the new compounds that contain a quaternised nitrogen atom can be obtained (1) by quaternising the corresponding dyestuffs that do not contain a quaternised nitrogen atom by treating them with alkylating agents: (2) by using quaternised diazo or coupling components, in particular those with aliphatic or cyclo ammmonium groups, or by using for the coupling already quaternised coupling components with benzoxazolium, benzimidazolium or benzthiazolium groups.

As alkylating or quaternising agents there may, for example, be used the methyl, ethyl, hydroxyethyl, cyanomethyl, n-propyl, n-butyl, β-cyanoethyl, benzyl esters of hydrogen chloride, hydrogen bromide, hydrogen iodide, dimethyl and diethyl sulphate, the methyl, β-chloroethyl, ethyl and butyl esters of benzenesulphonic acid or p-toluenesulphonic acid; the bromoacetic acid alkyl esters (with an alkyl radical of preferably 1 to 4 carbon atoms) are also suitable. Further alkylating agents are the following esters of hydrogen halide: hexyl bromide, benzyl bromide, chloroacetic nitrile, chloroacetamide, 2-chloro-propionic acid methyl ester, 3-chloro-propene, 2-chloro-ethynol, 3-chloropropanol, 6-chloro-hexanol, glycerine-chlorohydrin glycerine-dichloro-hydrin and 3-methoxy-propylchloride. Instead of certain substituted alkanol esters it is also possible to use their primary products, for example acrylonitrile or acrylamide in the presence of chlorine or hydrogen bromide instead of β-cyanoethyl or β-carbamoylethyl chloride or bromide. However, the preferred quaternising agent is dimethyl sulphate or benzyl chloride.

In accordance with the quaternising agents used suitable examples of the radical "alk" are: methyl, ethyl, propyl, n-butyl, n-pentyl, n-hexyl, -hydroxyhexyl, β-hydroxyethyl, chloroethyl, cyanoethyl, $H_2N$—$CO$—$CH_2$—, $Cl$—$CH_2$—$CH(OH)$-$CH_2$—, benzyl and methylbenzyl-, 3-hydroxypropyl-, carbamoylethyl, 3-methoxy-propyl, carboxymethylethyl and propenyl radicals.

The anion $A^-$ is to be understood as including both organic and inorganic ions, for example halogen ions, such as chloride, bromide or iodide ione, alkyl sulphate, sulphate, disulphate, perchlorate, phospho-tungstate, phosphotungsten molybdate, benzene- or naphthalene sulphonate, 4-chlorobenzene sulphonate, oxalate, maleinate, acetate, propionate, methane sulphonate, chloroacetate, toluene sulphonate or toluene benzoate ions.

These anions which are introduced according to the process of the invention can also be replaced by anion of other acids, for example phosphoric acid, acetic acid, oxalic acid, lactic acid, tartaric acid, maleic acid, crotonic acid, citric acid, nitric acid or benzoic acid. The dyestuffs can also be isolated in the form of complex salts with zinc or cadmium halides.

The alkylation is carried out appropriately by heating in an inert organic solvent, for example hydrocarbons such as benzene, toluene or xylene, halogenated hydrocarbons such as carbon tetrachloride, tetrachloroethane, chlorobenzene, o-dichlorobenzene, or nitrated hydrocarbons, such as nitromethane, nitrobenzene or nitronaphthalene, Acid anhydrides, acid amides or nitriles, such as acetic anhydride, dimethylformamide or acetonitrile or also dimethylsulphoxide, can also be used as solvents in the alkylation. Instead of a solvent, it is also possible to use a substantial excess of alkylating agent. However, in this case care must be taken that the mixture does not overheat to an excessive degree since the reaction is strongly exothermic. Despite this fact, it is necessary in most cases — especially in the presence of organic solvents — to heat the reaction mixture externally in order to initiate the reaction. In particular cases, the alkylation can also be carried out in aqueous medium or with the use of an alcohol, if necessary in the presence of small amounts of potassium iodide.

In case it is necessary to purify the salts, this is done appropriately by dissolving them in water, when, if desired, unreacted starting dyestuff can be filtered off as insoluble residue. By adding water soluble salts, for example sodium chloride, the dyestuff can be precipitated again from the aqueous solution.

As a rule, the non-quaternised dyestuffs are difficultly soluble or insoluble in water.

The new compounds, their mixtures with one another and their mixtures with other azo dystuffs are excellently suitable for dyeing and printing leather, wool, silk, cotton and above all, synthetic fibres such, for example, as acrylic or acrylonitrile fibres, polyacrylonitrile fibres and copolymers from acrylonitrile and other vinyl compounds, such as acrylic esters, acrylic amides, vinyl pyridines, vinyl chloride and vinylidene chloride: co-polymers from dicyanoethylene and vinyl acetate, and from acrylonitrile blook copolymers, fibres from polyurethane, polyolefines, such as basically modified polypropylene, polypropylene modified with nickel or unmodified polypropylene, cellulose triacetate and cellulose 2 ½-acetate, and especially fibres from polyamides, such as nylon-6, nylon-6,6 or nylon-12, and from aromatic polyesters, such as those from terephthalic acid and ethylene glycol.

For the dyeing in aqueous liquors the water-insoluble dyestuffs are appropriately used in finely distributed form and dyeing is carried out using dispersing agents, such as sulphite cellulose waste lye or synthetic detergents, or a combination of various wetting and dispersing agents. As a rule it is appropriate to convert the dyestuffs to be used before the dyeing into a dyestuff preparation that contains a dispersing agent and finely divided dyestuff in such a form that a fine dispersing results when the dyestuff preparation is diluted with water. Such dyestuff preparations can be obtained in known manner, for example by grinding the dyestuff in the dry or wet form with or without the addition of dispersing agents in the grinding process. After the wet grinding, dyestuff preparations are obtained by subsequent drying which consist of textile auxiliary and dyestuff.

Examples of dispersants of the non-ionic groups that can be used with advantage are: addition products of 8 moles of ethylene oxide with 1 mole of p-tert-.-octyl-phenol, of 15 resp. 6 mols of ethylene oxide with castor oil, of 20 mols of ethylene oxide with the alcohol $C_{16}H_{33}OH$, ethylene oxide addition products with di-[α-phenylethyl]-phenols, polyethylene oxide-tert.-dode-cyl-thioether, polyamino-polyglycol ether or addition products of 15 resp. 30 moles of ethylene oxide with 1 mole of the amine $C_{12}H_{25}NH_2$ or $C_{18}H_{37}NH_2$:

As anionic dispersants there may be mentioned: sulphuric acid esters of alcohols of the fatty series having 8 to 20 carbon atoms, of the ethyleneoxy adducts of the corresponding fatty acid amides, or of alkylated phenols having 8 to 12 carbon atoms in the alkyl radical: sulphonic acid esters with alkyl radicals having 8 to 20 carbon atoms, sulphation products of unsaturated fats and oils; phosphoric acid esters having 8 to 20 carbon atoms; fatty acid soaps, also alkylaryl sulphonates, condensation products of formaldehyde with napthalene-sulphonic acid and lignin sulphonate.

Suitable cationic dispersants are quaternary ammonium compounds that contain alkyl or aralkyl radicals having 8 to 20 carbon atoms.

In addition to the dispersants, the dyestuff preparations can contain organic solvents, especially solvents that boil above 100° C, which preferably are miscible with water, such as mono- and dialkylglycol ether, dioxane, dimethylformamide or dimethylacetamide, tetramethylenesulphone or dimethylsulphoxide. Dyestuffs, dispersant and solvent can with advantage be ground with one another. Instead of the dispersant, it is also possible to use only solvents; the dyestuff preparations, however, contain at least dispersant or solvent.

The polyester fibres are dyed from aqueous dispersion with the dyestuff according to the invention, which are difficulty soluble in water, according to the conventional processes for polyester materials. Polyesters of aromatic polycarboxylic acids with polyhydric alcohols are dyed preferably at temperatures of over 100° C under pressure. However, the dyeing can also be carried out at the boiling point of the dye bath in the presence of dyestuff carriers, for example phenylphenols, polychlorobenzene compounds or similar auxiliaries, or according to the thermosol process, that is to say padding with subsequent after-treatment with the application of heat, for example thermosetting, at 180°–210° C. Cellulose 2 ½-acetate fibres are dyed preferably at temperatures of 80°–85° C, whereas cellulose triacetate fibres are dyed advantageously at the boiling point of the bath. The use of dyestuff carriers is superfluous in dyeing cellulose 2 ½-acetate or polyamide fibres. Anthraquinone dyestuffs according to the invention can also be used for printing the materials mentioned according to conventional methods.

For the thermofixing of the dyestuff, the padded polyester material is heated to temperatures of above 100° C, for example between 180°–210° C, appropriately after previously drying it, for example on a warm current of air.

The dyeings obtained according to the instant process can be subjected to an after-treatment, for example by heating with an aqueous solution of an ion-free detergent.

According to the process of the present invention, the cited compounds can also be applied by printing instead of by impregnating. To this end, a printing paste, for example, is used which contains the finely dispersed dyestuff in addition to the usual auxiliaries used in the printing industry, such as wetting agents and binders.

The dyeing can furthermore be carried out, for example, in organic solvent liquor, such as in perchloroethylene, or by Dyblen Process as described hereunder: 10 Parts of dyestuff paste to 5% strength is stirred into a stock thickening, containing 80 parts of emulsion thickening and 10 parts of polyethylene glycol — 400, to get a printing paste. The polyester — cotton blend (66:33) is printed with above paste, dried to 70°–80° C and thermofixed at 205° C for 30 seconds. It is washed with cold water and soaped.

According to the process of the present invention, powerful dyeings and prints possessing good fastness properties are obtained, especially good fastness to thermosetting, sublimation, pleating, exhaust gas, cross-dyeing drycleaning and chloride, and good wet fastness properties, for example fastness to water, washing and perspiration.

It is also possible to use the new water-insoluble compounds for the spin dyeing of polyamides, polyesters and polyolefines. The polymers to be dyed are appropriately in the form of powder, grains or chips, as ready prepared spinning solution or mixed in the fused state with the dyestuff, which is introduced in the dry state or in the form of a dispersion or solution in a solvent that may be volatile. After the dyestuff has been uniformly distributed in the solution or the melt of the polymer, the mixture is processed in known manner by pouring, moulding or extruding to fibres, yarns, monofilaments, films and the like.

The following examples illustrate the invention, the parts and percentages being by weight and temperature as degrees centigrade unless otherwise stated.

Manufacture of the Coupling Components

Instruction 1

To a solution of 1.73 parts of sodium in 200 parts of absolute ethanol is added 12.5 parts of 2-mercaptobenzothiazole, the mixture boiled under reflux for 1 hour, cooled end 18.11 parts of N-ethyl-N-(α-chloroacetoxyethyl) aniline in 25 parts of ethanol, added. The mixture is boiled under reflux for 15 hours, precipitated sodium chloride fitered off and the bulk of the alcohol is removed by distillation. The residue is cooled, mixed with water and extracted with chloroform, extract dried over sodium sulphate and solvent evaporated off to furnish N-ethyl-N-(benzthiazolyl-2-thioacetoxyethyl) aniline having the formula

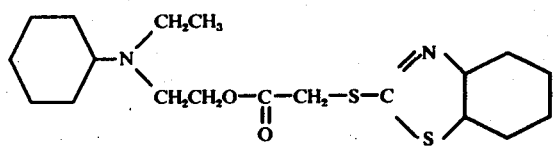

Instruction-2

To a solution of 1.58 parts of sodium in 200 parts of absolute ethanol is added 11.5 parts of 2-mercaptobenzothiazole and the mixture boiled under reflux for 1 hour. It is cooled and 17.6 parts of N-ethyl-N-(α-chloroacetoxyethyl) m-toluidine in 25 parts of ethanol are added to the above solution. The mixture boiled under reflux for 15 hours and worked up in the manner described in Instruction 1 to furnish N-ethyl-N-(benzthiazolyl-2-thioacetoxyethyl)-m-toluidine having the formula

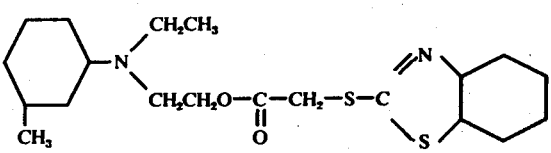

Instruction 3

To a solution of 1.53 parts of sodium in 250 parts of absolute ethanol, 10.06 parts of 2-mercaptobenzoxazole are added and the mixture boiled under reflux for one hour, cooled and 17.0 parts of N-ethyl-N-(α-chloroacetoxyethyl)-m-toluidine in 25 parts of ethanol are added to the above solution. The mixture is boiled under reflux for 15 hours, and then worked up in the manner described in Instruction-1 to furnish N-ethyl-N-(benzoxazolyl-2-thio acetoxyethyl) m-toluidine m.p. 73° C.

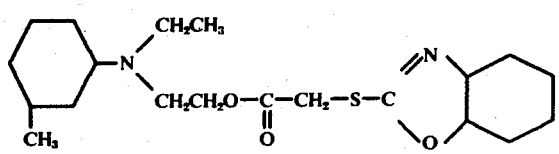

Instruction-4

To a solution of 1.85 parts of sodium in 250 parts of absolute ethanol. 12.2. parts of 2-mercaptobenzoxazole are added and the mixture boiled under reflux for 1 hour. It is cooled and 19.5 parts of N-ethyl-N(α-chloroacetoxyethyl) aniline in 25 parts of ethanol are added to the above solution. The mixture is boiled under reflux for 18 hours and worked up in the manner described in Instruction-1 to furnish N-ethyl-N-(benzoxazolyl-2-thio-acetoxyethyl) aniline having the following formula

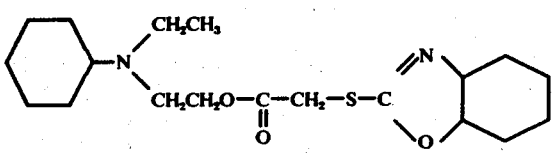

Instruction 5

10 parts of sodium salt of 2-mercaptobenzoxazole and 13.32 parts of N-(2-cyanoethyl)-N-(α-chloroacetoxyethyl)-aniline in 200 parts of xylene and 40 parts of dimethyl formamide is boiled under reflux for 24 hours. It is worked up in the manner described in Instruction-1 to furnish N-(2-cyanoethyl)-N-(benzoxazolyl-2-thioacetoxy ethyl) aniline having the formula

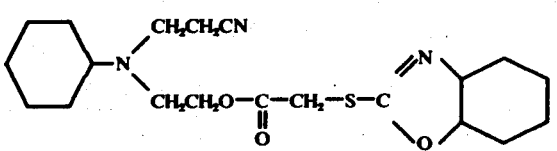

Instruction-6

10.5 Parts of sodium salt of 2-mercapto benzothiazole and 13.32 parts of N-(2-cyanoethyl)-N-(α-chloroacetoxyethyl) aniline are added in 200 parts of xylene and 40 parts of dimethylformamide. The mixture is boiled under reflux for 24 hours. It is worked up in the manner described in Instruction-1 to funish N-(2-cyanoethyl)-N-(benzothiazolyl-2-thioacetoxy ethyl) aniline having the following formula

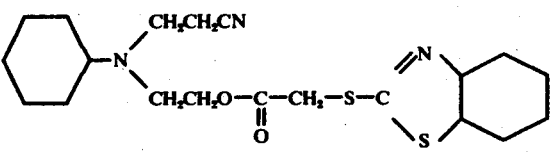

Instruction-7

3.33 Parts of sodium are dissolved in 400 parts of absolute ethanol. 21.9 parts of 2-mercaptobenzoxazole are added to the above solution. The mixture is boiled under reflux for one hour. It is cooled and 37.00 parts of N-ethyl-N-(β-chloropropionyloxyethyl)aniline in 25 parts of ethanol are added to the above solution. The mixture is boiled under reflux for 15 hours. It is worked up in the manner as described in Instruction-1 to furnish N-ethyl-N-(benzoxazolyl-2-thiopropionyloxyethyl) aniline having the following formula

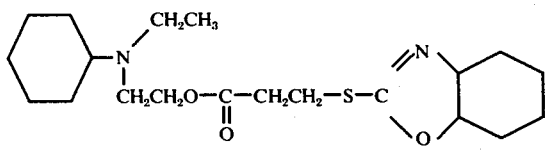

and can be crystallised from alcohol, m.p. 90°.

Instruction-8

To a solution of 1.53 parts of sodium in 250 parts of absolute ethanol, 10.1 parts of 2-mercaptobenzoxazole are added and the mixture boiled under reflux for one hour. It is cooled and 18.00 parts of N-ethyl-N-(β-chloropropionyloxyethyl) m-toluidine in 25 parts of ethanol added and the mixture boiled under reflux for 20 hours. It is worked up in the manner described in Instruction-1 to furnish N-ethyl-N-(benzoxazolyl-2-thiopropionyloxyethyl)m-toluidine having the following formula

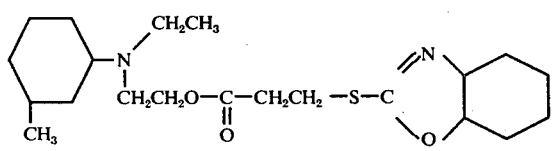

and can be crystallised from ethanol, m.p. 97°.

Instruction 9

To a solution of 2.36 parts of sodium in 400 parts of absolute ethanol, 17.16 parts of 2-mercaptobenzthiazole are added and the mixture boiled under reflux for one hour. It is cooled and 26.8 parts of N-ethyl-N-(α-chloro-acetoxyethyl)-m-nitroaniline in 50 parts of ethanol added and the mixture boiled under reflux for 20 hours. It is worked up in the usual manner as described under Instruction-1 to furnish N-ethyl-N-(benzthiazolyl-2-thioacetoxyethyl)m-nitroaniline having the following formula

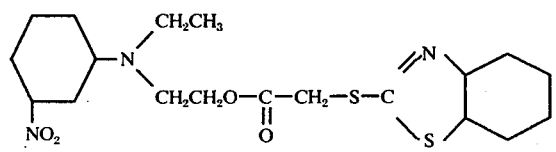

which after crystallisation from ethanol melts at 98°.

4.17 Parts of N-ethyl-N-(benzthiazolyl-2-thioacetoxyethyl)m-nitroaniline are dissolved in 75 parts of absolute ethanol and 25 parts of acetic anhydride and hydrogenated at 45° using 10% Pd/C as catalyst. The catalyst is filtered off and worked up in the usual manner to furnish N-ethyl-N-(benzthiazolyl-2-thio acetoxyethyl) m-acetamido aniline having the formula

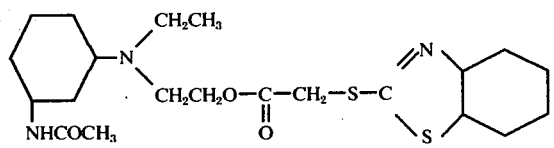

Instruction-10

To a solution of 2.0 parts of sodium in 250 parts of absolute ethanol is added 14.72 parts of 2-mercaptobenzothiazole, the mixture boiled under reflux for 1 hour, cooled and 25.08 parts of N-acetoxyethyl-N-(α-chloroacetoxyethyl) m-toluidine in 40 parts of absolute ethanol, added. The mixture is boil boiled under reflux for 15 hours, precipitated sodium chloride filtered off and the bulk of the alcohol is removed by distillation. The residue is cooled, mixed with water and extracted with chloroform, extract dried over sodium sulphate and solvent evaporated off to furnish N-acetoxyethyl-N-(benzthiazolyl-2-thioacetoxyethyl) m-toluidine having the formula

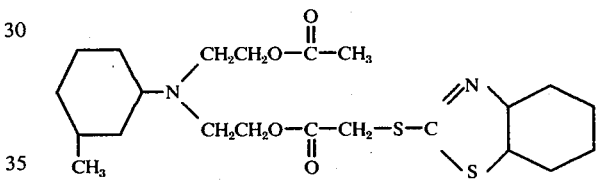

Instruction-11

To a solution of 11.16 parts of N-ethyl-N (benzthiazolyl-2-thio acetoxy ethyl) aniline in 250 parts of chlorobenzene is added a solution of 6.58 parts of freshly distilled dimethyl sulphate in 30 parts of chlorobenzene dropwise at 90°. The mixture is then stirred for 6 hours at 115°–120°. After cooling and filtering, the filter cake is dissolved in 200 parts of hot water and filtered. The filtrate contains the coupling component of the formula

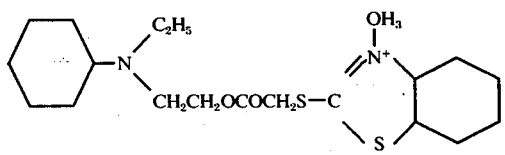

and is used directly for the coupling.

Manufacture of the Azo Compounds

EXAMPLE 1

1.73 Parts of 2-chloro-4-nitro aniline are diazotised with a mixture of 20 parts by volume of concentrated sulphuric acid and 1 part of sodium nitrite. The excess nitrous acid is destroyed with urea and the reaction mixture is filtered. The resulting solution is coupled at 5° to 10° with 3.72 parts of N-ethyl-N-(benzthiazolyl-2-thio-acetoxyethyl) aniline in a mixture of 40 parts of alcohol and 200 parts of water. The solution is stirred for 5 hours until the coupling is complete. The pH value is then adjusted to 4 to 5 with 4N sodium acetate solution at a temperature below 10° and the dyestuff is 1.0 part of sodium nitrite is added in ½ hour to the above solution at 0° to 5° and the stirring is continued at this temperature for 3 hours. It is coupled with 3.70 parts of N-ethyl-N-(benzoxazolyl-2-thioacetoxyethyl) m-toluidine dissolved in a mixture of acetic acid and propionic acids. The dye solution is diluted with ice and the dyestuff of the formula

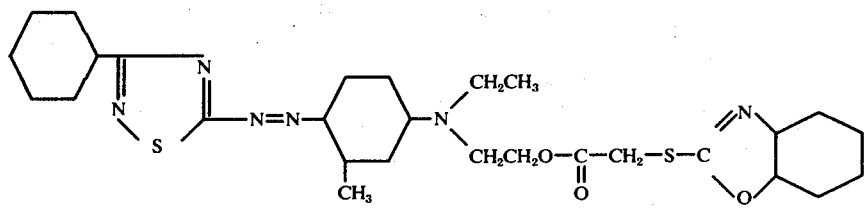

subsequently filtered off and washed with large amount of water, if necessary, the dyestuff is reprecipitated from acetone. The resulting dyestuff corresponds to the formula is isolated. It gives Bluish-Red shades on polyester fibre.

EXAMPLE 4

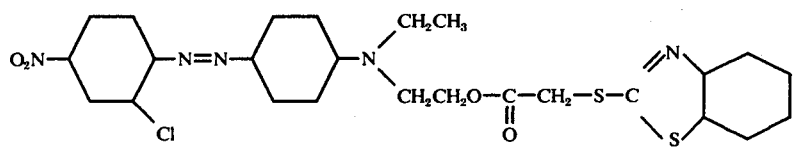

and dyes polyester fibres in Red shades possessing excellent properties of fastness when applied in the form of an aqueous dispersion.

EXAMPLE 2

1.64 parts of 2-cyano-4-nitro aniline are diazotised in the manner described above, but 4 parts of volume of acetic acid are added. The filtered solution of the diazonium compound is coupled with 3.86 parts of N-ethyl-N-(benzthiazolyl-2-thioacetoxyethyl)m-toluidine in a mixture of 40 parts of alcohol and 20 parts of water, as above. The resulting dyestuff of the formula 1.73 parts of 2-chloro-4-nitroaniline are diazotised in the manner described in example 1 and the filtered solution of the diazonium salt is coupled with 3.97 parts of N-(2-cyanoethyl)-N-(benzothiazolyl-2-thioacetoxy ethyl) aniline in a mixture of 100 parts of acetic acid and 50 parts of propionic acid. It is worked up in the usual manner to give a dyestuff having the formula

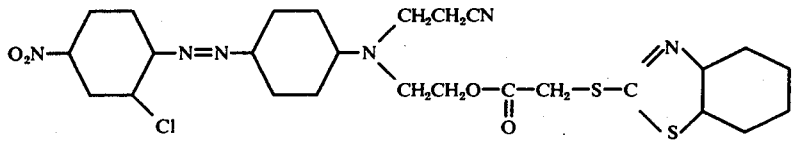

which dyes polyester fibres in Yellowish-Red shades possessing excellent properties of fastness when applied in the form of a aqueous dispersion.

EXAMPLE 5

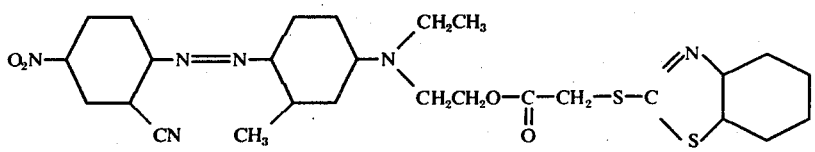

dyes polyester fibres in violet shades having very good fastness properties.

EXAMPLE 3

1.77 Parts of 2-amino-4-phenyl-1,3,5-thiadiazole dissolved in 25 parts of ortho phosphoric acid with 0.1 part of potassium bromide is kept at 0° to 5° for ½ hour.

2.1 parts of 2-chloro-4-methylsulfonyl aniline are dissolved in 20 parts of nitrosylsulphuric acid and diazotised as in Example 1. The filtered solution of the diazonium salt is coupled with 3.84 parts of N-ethyl-N(benzoxazolyl-2-thiopropionyl oxyethyl) m-toluidine dissolved in a mixture of acetic acid and propionic acid. The coupling is completed and the dyestuff of the formula

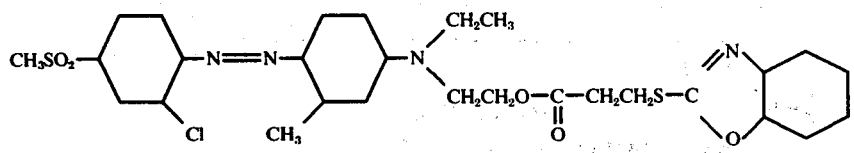

is isolated. It dyes polyester fibre Reddish-orange shade of good fastness properties.

EXAMPLE 6

1.73 Parts of 2-chloro-4-nitro aniline are diazotised in the manner described in Example 1 and the filtered solution of the diazonium salt is coupled with 4.29 parts of N-ethyl-N-(benzthiazolyl-2-thioacetoxyethyl)m-acetamide aniline in a mixture of 100 parts of acetic acid and 50 parts of propionic acid. It is worked up in the usual manner to give dyestuff having the formula which dyes polyester fibres in bluish-Red shades possessing excellent properties of fastness when applied in the form of aqueous dispersion.

The following which dye polyester fibres in the indicated shades can be manufactured in an identical manner.

| Dyestuff | Shade |
|---|---|
| (structure with Br, O₂N, CN, CH₃, N=N, CH₂CH₃, CH₂CH₂O—C(=O)—CH₂—S—C, benzothiazole ring with S) | Bluish-Violet |
| (structure with Br, O₂N, CN, CH₃, N=N, CH₂CH₃, CH₂CH₂O—C(=O)—CH₂—S—C, benzoxazole ring with O) | Bluish-Violet |

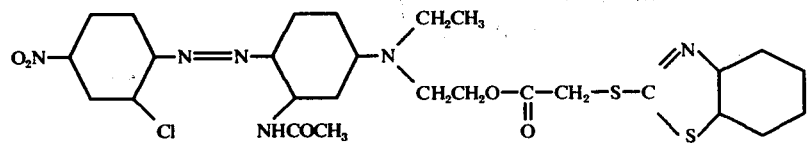

The dyestuffs listed in the following table are obtained analogously if the diazonium compound of the diazo components listed in Column I is coupled with the coupling components listed in Column II. The dyestuffs dye polyester fibres in the shades indicated in Column III.

| No. | I | II | III |
|---|---|---|---|
| 1. | 2-Cyano-4-nitro-aniline | (cyclohexyl-N(CH₂CH₃)(CH₂CH₂OCOCH₂S—C benzothiazole)) | Bluish-Red |
| 2. | 2,6-Dichloro-4-nitro-aniline | " | Brown |
| 3. | 2-Cyano-4-nitro-6-bromo-aniline | " | Violet |
| 4. | 2-Amino-6-methyl-sulfonyl benzthiazole | " | Bluish-Red |

-continued

| No. | I | II | III |
|---|---|---|---|
| 5. | 2-Chloro-4-nitro-aniline | [structure: cyclohexyl with CH₃, N(CH₂CH₃)(CH₂CH₂OCOCH₂S—C=N), cyclohexane with S] | Bluish-Red |
| 6. | 2-Chloro-4-ethyl-sulfonyl-aniline | " | Reddish-Orange |
| 7. | 2-cyano-4-nitro-6-chloroaniline | " | Bluish-Violet |
| 8. | 2-Amino-5-nitrothiazole | " | Bluish-Violet |
| 9. | 2-Amino-4-phenyl-1,3,5,thiadiazole | " | Bluish-Red |
| 10. | 4-Nitro-aniline | [structure: cyclohexyl-N(CH₂CH₃)(CH₂CH₂OCOCH₂S—C=N), cyclohexane with O] | Yellowish-Red |
| 11. | 2-Cyano-4-nitro-aniline | " | Bordeaux |
| 12. | 2,6-Dichloro-4-nitroaniline | " | Scarlet |
| 13. | 2-Cyano-4-nitro-6-bromoaniline | " | Violet |
| 14. | 2-Methoxy-4-nitroaniline | " | Red |
| 15. | 2-Amino-5-phenyl-1,3,4-thiadiazole | [structure: cyclohexyl with CH₃, N(CH₂CH₃)(CH₂CH₂OCOCH₂S—C=N), cyclohexane with O] | Red |
| 16. | 2-Amino-6-methyl sulfonyl-benzthiazole | " | Bluish-Red |
| 17. | 2,6-Dichloro-4-nitroaniline | " | Reddish-Brown |
| 18. | 2-Cyano-4-nitro-6-chloro aniline | " | Bluish-Violet |
| 19. | 2-Chloro-4-methyl sulfonyl aniline | [structure: cyclohexyl-N(CH₂CH₂CN)(CH₂CH₂OCOCH₂S—C=N), cyclohexane with O] | Yellowish-orange |
| 20. | 2-Chloro-4-nitro aniline | " | Yellowish-red |
| 21. | 2,6-Dichloro-4-nitroaniline | " | Reddish orange |
| 22. | 2-Cyano-4-nitro aniline | " | Red |
| 23. | 2-Cyano-4-nitro 6-bromo aniline | " | Bluish-Red |
| 24. | 5-Amino-4-nitro 3-methyl-1,2-isothiazole | " | Reddish-Violet |

-continued

| No. | I | II | III |
|---|---|---|---|
| 25. | 2,6-Dichloro-4-nitro aniline | [structure: cyclohexyl-N(CH₂CH₂CN)(CH₂CH₂OCOCN₂S—C=N-cyclohexyl with S)] | Reddish-orange |
| 26. | 2-Chloro-4-ethyl sulfonyl aniline | " | Yellowish orange |
| 27. | 2,4-Dinitro-6-chloro-aniline | [structure: cyclohexyl-N(CH₂CH₃)(CH₂CH₂OCOCH₂CH₂S—C=N-cyclohexyl with O)] | Bluish-Violet |
| 28. | 2-Amino-6-nitro benzthiazole | " | Reddish-Violet |
| 29. | 2,4-Dinitro-aniline | [structure: 3-methylcyclohexyl-N(CH₂CH₃)(CH₂CH₂OCOCH₂CH₂—S—C=N-cyclohexyl with O)] | Bluish-violet |
| 30. | 2-Amino-5-nitrothiazole | " | Blue |
| 31. | 2-Amino-4-phenyl 1,3,5-thiadiazole | " | Red |
| 32. | 2-Chloro-6-bromo-4-nitro aniline | [structure: cyclohexyl-N(CH₂CH₃)(CH₂CH₂OCOCH₂CH₂S—C=N-cyclohexyl with S)] | Orange |
| 33. | 2-Cyano-4-nitro aniline | " | Reddish-Violet |
| 34. | 2-Methyl-4-nitro aniline | [structure: 3-methylcyclohexyl-N(CH₂CH₃)(CH₂CH₂OCOCH₂CH₂S—C=N-cyclohexyl with O)] | Red |
| 35. | 2-Amino-5-cyanothiazole | " | Reddish-Violet |
| 36. | 2-Cyano-4-nitro-6-bromo aniline | [structure: 3-methylcyclohexyl-N(CH₂CH₂CH₃)(CH₂CH₂OCOCH₂S—C=N-cyclohexyl with S)] | Bluish Violet |
| 37. | 2-Chloro-4-methyl sulfonyl aniline | " | Reddish orange |
| 38. | 2,6-Dichloro-4-nitroanilino | [structure: cyclohexyl-N(C₄H₉)(CH₂CH₂OCOCH₂—S—C=N-cyclohexyl with S)] | Reddish-brown |

-continued

| No. | I | II | III |
|---|---|---|---|
| 39. | 2-Methyl sulfonyl-4-nitroaniline | 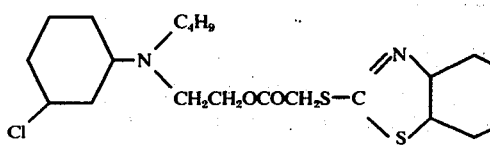 | Bluish red |
| 40. | Amino-azo-benzene | '' | Reddish orange |
| 41. | 5-Amino-3-methyl 1-phenyl pyrazole | '' | Orange |
| 42. | 2-Amino-5-acetyl--3-nitro thiophene | '' | Blue |
| 43. | 2-Cyano-4-nitro-aniline | 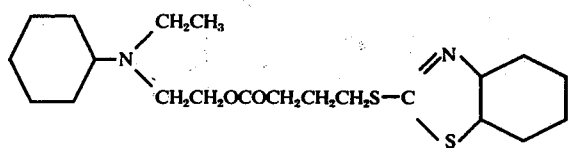 | Reddish-violet |
| 44. | 2-Chloro-4-nitro-6-bromo-aniline | 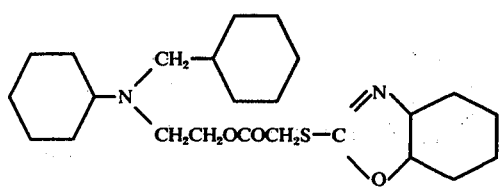 | Orange |
| 45. | 2-Cyano-4-nitro aniline | 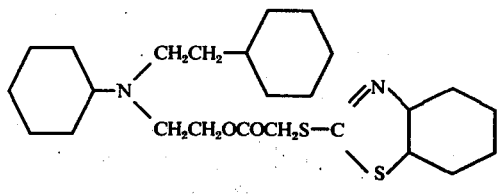 | Red |
| 46. | 2-Amino-4-phenyl 1,3,5-thiadiazole | 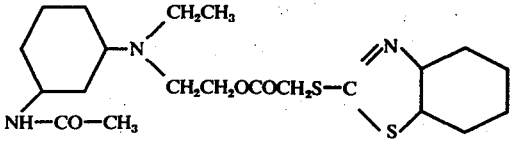 | Bluish-red |
| 47. | 2,4-Dinitro-6-cyano aniline | '' | Reddish-Blue |
| 48. | 2-Cyano-4-nitroaniline | '' | Bluish-Violet |
| 49. | 2,6-Dicyano-4-nitro aniline | '' | Reddish-blue |
| 50. | 4-Nitroaniline | '' | Red |
| 51. | 3-Amino-5-nitro benzo-1,2-isothiazole | '' | Blue |
| 52. | 4-Amino-2,5-dichloro-benzene dimethyl-sulphamide | '' | Red |
| 53. | 2,6-Dichloro-4-cyano aniline | 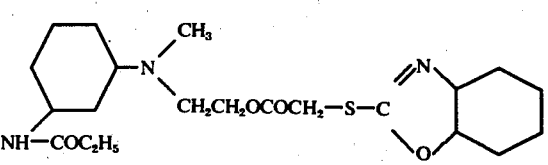 | Red |
| 54. | 2,6-Dicyano-4-nitro aniline | '' | Blue |
| 55. | 4-Carbathoxy-2-methyl-4-amino azo benzene | '' | Yellowish-Red |

-continued

| No. | I | II | III |
|---|---|---|---|
| 56. | 2,4-Dinitro-6-chloro aniline | (structure) | Blue |
| 57. | 2,4-Dinitro-6-bromoaniline | (structure) | Blue |
| 58. | 2-Chloro-4-nitro aniline | (structure) | Red |
| 59. | 2-Cyano-4-nitroaniline | " | Reddish-Violet |
| 60. | 2-Amino-4-phenyl 1,3,5-thiadiazole | " | Red |
| 61. | 2,6-Dichloro-4-nitroaniline | " | Reddish-orange |
| 62. | 4-Amino-3-chloro benzene chloroethyl | (structure) | Red |
| 63. | 4-Amino-ω-chloro acetophenone | (structure) | Yellowish-Red |
| 64. | 3-Amino-pyridine | " | Orange |
| 65. | 2-Bromo-4-nitro-6-cyano aniline | (structure) | Violet |
| 66. | 2-Amino-5-phenyl-1,3,4-thiadiazole | " | Yellowish Red |
| 67. | 4-Amino-benzoic acid methoxy ethyl ester | (structure) | Orange |

-continued

| No. | I | II | III |
|---|---|---|---|
| 68. | 2-Amino-5-nitrothiazole | " | Reddish-Blue |
| 69. | 2-Chloro-4-nitroaniline | [structure with cyclohexyl-N(CH₂CH₂OCOCH₂O-cyclohexyl)(CH₂CH₂OCOCH₂S—C=N-cyclohexyl fused with S)] | Yellowish-Red |
| 70. | 2-Amino-6-cyano benzthiazole | [structure with cyclohexyl-N(CH₂CH₂COOC₂H₅)(CH₂CH₂OCOCH₂S—C=N-cyclohexyl fused with S)] | Red |
| 71. | 2-Methyl sulphonyl-4-nitro aniline | " | Red |
| 72. | 2-Cyano-4-chloro aniline | [structure with cyclohexyl-N(CH₂CH₂COO-cyclohexyl)(CH₂CH₂OCOCH₂S—C=N-cyclohexyl with NH)] | Orange |
| 73. | 4-Aminobenzoic acid ethoxy ethyl ester | [structure with cyclohexyl-N(CH₂CH₂CO-cyclohexyl)(CH₂CH₂OCOCH₂S—C=N-cyclohexyl with N-C₂H₅)] | Orange |
| 74. | 4-Amino-2,5-dimethoxy azo benzene | [structure with cyclohexyl-N(CH₂CH₂CO—CH₃)(CH₂CH₂OCO—CH₂S—C=N-cyclohexyl with NH-CO-CH₃ and NH)] | |
| 75. | 2-Methyl-4-nitro aniline | [structure with cyclohexyl-N(C₂H₄O-cyclohexyl)(CH₂CH₂OCOCH₂—S—C=N-cyclohexyl fused with S)] | Orange |
| 76. | 4-Nitro-2-chloro-4-amino azo-benzene | [structure with cyclohexyl-N(C₂H₄OC₂H₅)(CH₂CH₂OCOCH₂S—C=N-cyclohexyl with CN and NH)] | Yellowish-Red |

| No. | I | II | III |
|-----|---|----|-----|
| 77. | 4-Amino-ω-chloro acetophenone | 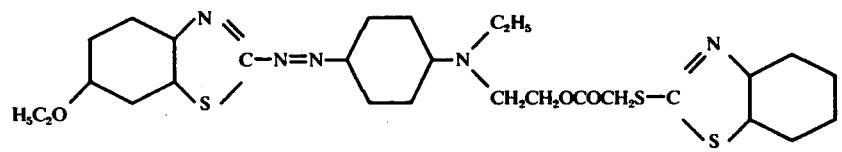 | Orange |

Dyeing instruction (HT-Process)

1 Part of the dyestuff obtained above is ground wet with 2 parts of a 50% strength aqueous solution of the sodium salt of dinaphthylmethanedisulphonic acid and dried. This dyestuff preparation is stirred with 40 parts of a 10% aqueous solution of the sodium salt of N-benzyl-μ-heptadecylbenzimidazole disulphonic acid and 4 parts of 40% acetic acid solution are added. 4000 parts of a dye bath are thereafter prepared by dilution with water.

100 Parts of a cleaned polyethylene terephthalate fibre material are introduced into this bath at 50°, the temperature is raised to 120° to 130° in half an hour and dyeing is carried out for one hour in a closed vessel at this temperature. A red dyeing of excellent fastness to light and to sublimation is obtained. Unless otherwise specified, the shades mentioned in the examples were obtained according to the HT process.

EXAMPLE 7

3 parts of sodium nitrite are strewn into 30 parts of concentrated sulphuric acid at 0°. The mixture is then heated to 65° until dissolution is complete. After cooling the solution to 0°, 30 parts by volume of glacial acetic acid and propionic acid (:1) are added dropwise while cooling 5.82 parts of 6-ethoxy-2-amino-benzthiazole (dissolved in 50 parts of the glacial acetic acid/propionic acid mixture) and then dropped in while cooling and the mixture is stirred for 3 hours at this temperature. 3.5 Parts of urea are then added slowly and finally the solution is slowly added to the solution of 11.16 parts of N-ethyl-N(benzthiazolyl-2-thioacetoxy ethyl) aniline in 150 parts of glacial acid.

The batch is stirred for 3 hours at 0°–10° and finally neutralised with sodium acetate solution. The dyestuff of the formula

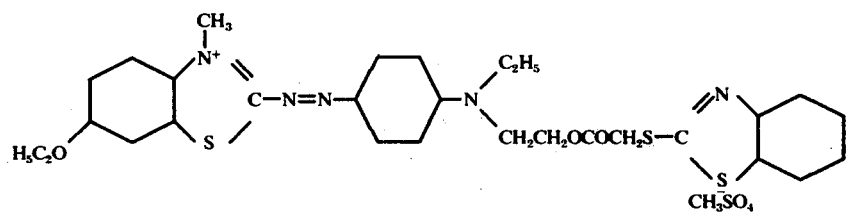

is obtained.

The methylation of this dyestuff (5.77 parts) with 4.0 parts of freshly distilled dimethyl sulphate in chlorobenzene at 90°–95° and subsequent stirring at 95°–100° for 4 hours yields the dyestuff of the formula which is obtained by salting it out from an aqueous solution and dyes polyacrylic fibres in blue shades possessing good fastness properties.

Dyestuffs prepared from the diazo components listed in Column I and the coupling components listed in Column II are obtained analogously. After alkylation with the alkylating agents listed in Column III, the dyestuffs yield cationic dyestuffs which dye polyacrylic fibres in the shades indicated in Column IV.

| No. | I | II | III | IV |
|-----|---|----|-----|-----|
| 1. | 2-amino-6-ethoxy-benzthiazole | | | Dimethyl sulphate |

-continued

| No. I | II | III | IV |
|---|---|---|---|
| 2. | 3-Amino-1,2,4-triazole | 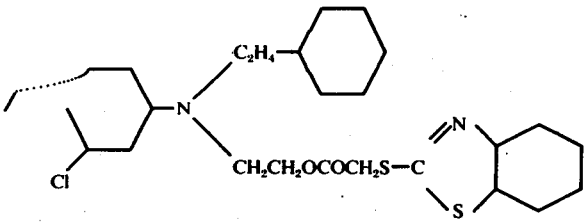 | Toluene sulphonic acid methyl ester |
| 3. | 2-Amino-5-methyl-1,3,4-thiadiazole | 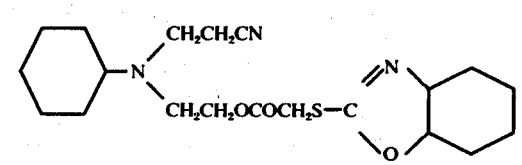 | Diethyl sulphate |
| 4. | 3-Amino-pyridine | 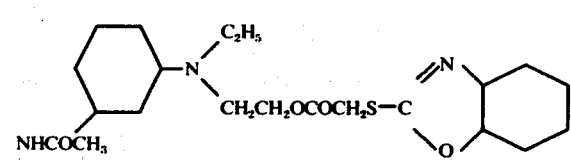 | Diethyl sulphate |
| 5. | 4-Amino-ω-morpholino acetophenone | 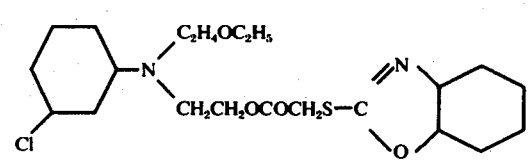 | Benzyl chloride |
| 6. | 4-Nitro-2-piperidino ethoxy aniline | 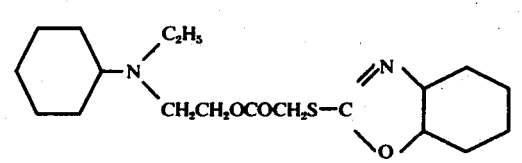 | Benzene sulphonic acid ethyl ester |

Dyeing Instruction

One Part of the obtained dyestuff of the formula

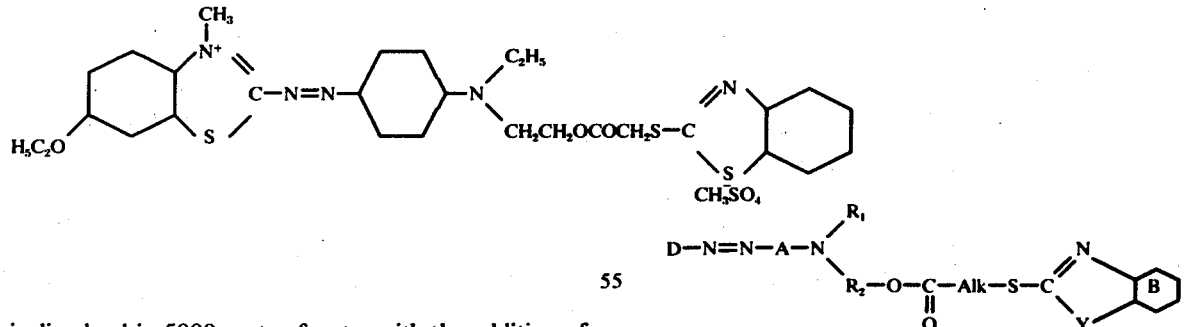

is dissolved in 5000 parts of water with the addition of 2 parts of 40% acetic acid. 100 Parts of dried yarn from polyacrylonitrile staple fibres are introduced into this dye bath at 60°, the temperature is raised within half an hour to 100° and dyeing is carried out for one hour at boiling temperature. The dyed goods are then thoroughly rinsed and dried. A blue dyeing possessing very good fastness to light, sublimation and washing is obtained.

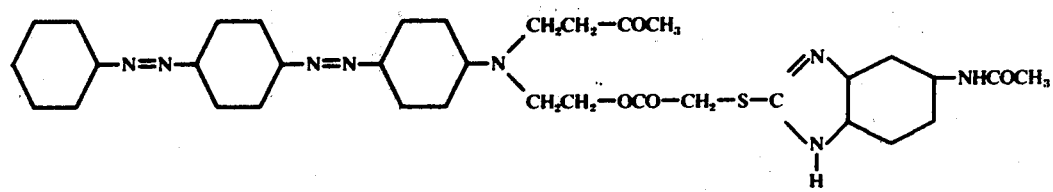

I claim:

1. An azo compound that is free from sulphonic acid groups of the formula $$D-N=N-A-N\begin{matrix}R_1\\R_2-O-C-Alk-S-C\\\parallel\\O\end{matrix}$$

in which D represents the radical of a diazo component, A represents an optionally substituted, 1,4-phenylene radical, $R_1$ represents an optionally substituted alkyl radical, $R_2$ represents an optionally substituted alkylene radical, Alk represents an alkylene radical of 1–4 carbon atoms and Y represents an imino group, a sulphur atom or an oxygen atom and ring B may be substituted by bromine, fluorine, chlorine atoms, cyano, nitro, trifluoromethyl, alkyl, alkoxy, acylamino, acyloxy, carbalkoxy, optionally N-alkylated carbamoyl and optionally N-alkylated sulphamoyl groups and by a benzo residue.

2. A compound according to claim 1 of the formula

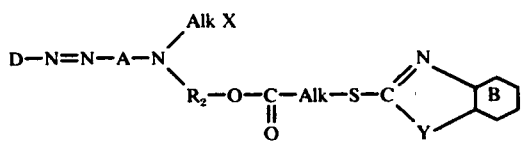

in which X is hydrogen, a hydroxyl, a halogen, cyano or an organic radical.

3. A compound according to claim 2 of the formula

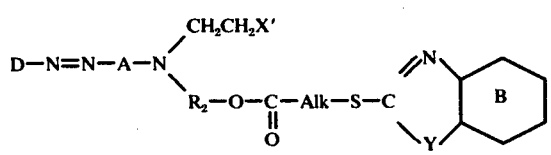

in which X' is an alkoxy or acyloxy radical of an organic acid, a lower alkyl radical, a hydrogen atom, or a cyano group.

4. A compound according to claim 1, wherein Y is a sulphur atom.

5. A compound according to claim 1, wherein Y is an oxygen atom.

6. A compound according to claim 1, wherein Y is an optionally substituted —NH group.

7. A compound according to claim 1, wherein the radical A corresponds to the formula

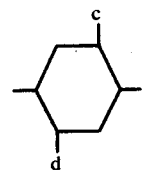

and is bonded to the azo bridge with the left-hand free bond, and c and d each represents a hydrogen or chlorine atom, a lower alkyl group or a lower alkoxy group, phenoxy or phenylthio group and d in addition may optionally represent a bromine atom, a trifluoromethyl group or an optionally substituted acylamino group.

8. A compound according to claim 7, wherein the radical D is a radical of benzene, benzthiazole, thiazole, imidazole, isothiazole, benzisothiazole, triazole, or thiadiazole.

9. A compound according to claim 7, which are free of ion-forming substituents.

10. A compound according to claim 7 which contain at least one quarternised nitrogen atom.

11. A compound according to claim 10 wherein the radical D of the diazo component is quaternised.

12. A azo compound according to claim 7, wherein $R_2$ is ethylene.

13. A dyestuff as claimed in claim 8 of the formula

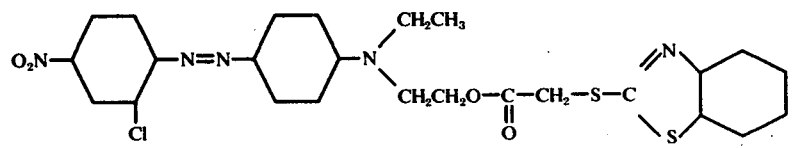

14. A dyestuff as claimed in claim 8 of the formula

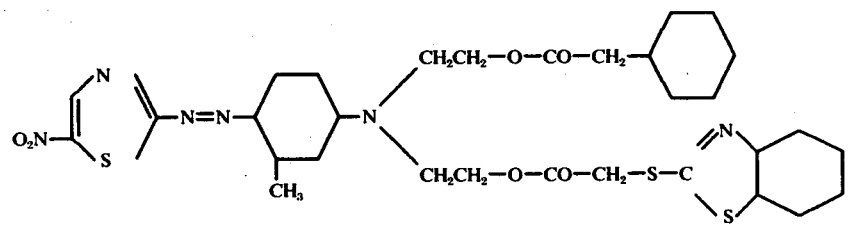

15. A dyestuff as claimed in claim 11 of the formula

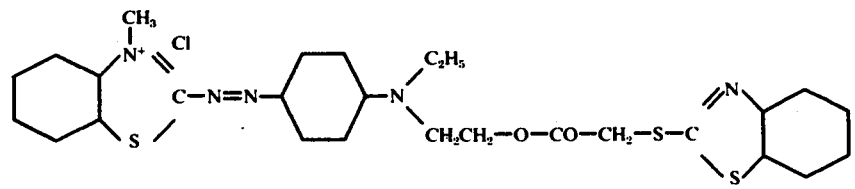

16. A dyestuff as claimed in claim 8 of the formula